(12) United States Patent
Kishi et al.

(10) Patent No.: US 8,002,694 B2
(45) Date of Patent: Aug. 23, 2011

(54) MASTER-SLAVE MANIPULATOR SYSTEM

(75) Inventors: Kosuke Kishi, Mito (JP); Makoto Hashizume, Fukuoka (JP)

(73) Assignees: Hitachi, Ltd., Tokyo (JP); Kyushu University, Fukuoka (JP)

( * ) Notice: Subject to any disclaimer, the term of this patent is extended or adjusted under 35 U.S.C. 154(b) by 719 days.

(21) Appl. No.: 12/019,668

(22) Filed: Jan. 25, 2008

(65) Prior Publication Data
US 2008/0234866 A1 Sep. 25, 2008

(30) Foreign Application Priority Data

Mar. 20, 2007 (JP) .................... 2007-072447

(51) Int. Cl.
*A61B 17/00* (2006.01)
(52) U.S. Cl. ........ 600/103; 600/228; 600/229; 600/235; 600/372; 600/424; 606/1
(58) Field of Classification Search .......... 606/139, 606/130, 1, 32; 318/568.21, 568; 700/245; 600/109, 431, 103, 228, 235, 372, 424, 229; 128/898; 601/1; 901/2
See application file for complete search history.

(56) References Cited

U.S. PATENT DOCUMENTS

| | | | |
|---|---|---|---|
| 6,522,906 | B1 | 2/2003 | Salisbury, Jr. et al. |
| 7,395,249 | B2 * | 7/2008 | Wang et al. ............. 706/14 |
| 7,741,802 | B2 * | 6/2010 | Prisco et al. ........... 318/568.11 |
| 2005/0107808 | A1 * | 5/2005 | Evans et al. ............ 606/139 |
| 2006/0241414 | A1 * | 10/2006 | Nowlin et al. ........... 600/431 |
| 2007/0005045 | A1 * | 1/2007 | Mintz et al. ............ 606/1 |
| 2007/0013336 | A1 * | 1/2007 | Nowlin et al. .......... 318/568.21 |
| 2007/0083098 | A1 * | 4/2007 | Stern et al. ............. 600/407 |
| 2007/0142824 | A1 * | 6/2007 | Devengenzo et al. ....... 606/1 |
| 2008/0033240 | A1 * | 2/2008 | Hoffman et al. ......... 600/109 |
| 2008/0046122 | A1 * | 2/2008 | Manzo et al. ........... 700/245 |
| 2008/0215056 | A1 * | 9/2008 | Miller et al. ........... 606/80 |

FOREIGN PATENT DOCUMENTS

| | | |
|---|---|---|
| JP | 7-328016 | 12/1995 |
| JP | 7-328971 | 12/1995 |
| JP | 2003-265500 | 9/2003 |

OTHER PUBLICATIONS

European Search Report, dated Mar. 1, 2011, issued in corresponding European Patent Application No. EP 08 00 1129.

* cited by examiner

*Primary Examiner* — Ronnie Mancho
(74) *Attorney, Agent, or Firm* — Antonelli, Terry, Stout & Kraus, LLP.

(57) ABSTRACT

In a master-slave manipulator system, manipulation device can be manipulated intuitively even when clutch manipulation is performed. A master-slave manipulator system includes: mode switching device for switching between a master-slave mode, in which the slave manipulator is controlled, and an observation device visual field tracking clutch mode, in which transmission of an operation command to the slave manipulator from the manipulation device is cut off to move the manipulation device to an optional position and orientation; a switching unit control section that reads a signal of the mode switching device to forward a mode signal to the manipulation device control section; and a visual field transform section that forwards a third control command to the manipulator control section and forwards a fourth control command to the visual field change control section on the basis of an operation command read by the manipulation device control section at the time of the observation device visual field tracking clutch mode so as to make an agreement between a direction of motion of an image of the slave manipulator displayed on the display device and a direction of manipulation of the manipulation device.

6 Claims, 12 Drawing Sheets

FIG.6

|  | | MASTER-SLAVE MODE SWITCHING UNIT | |
|---|---|---|---|
|  | | ON | OFF |
| ENDOSCOPE MODE SWITCHING UNIT | ON | ENDOSCOPE VISUAL FIELD TRACKING MASTER-SLAVE MODE | ENDOSCOPE VISUAL FIELD TRACKING CLUTCH MODE |
|  | OFF | MASTER-SLAVE MODE | CUTTING-OFF OF MASTER-SLAVE CONNECTION (CONVENTIONAL CLUTCH MODE) |

MASTER-SLAVE MANIPULATOR SYSTEM

BACKGROUND OF THE INVENTION

The present invention relates to a master-slave manipulator system.

Many master-slave manipulator systems have been developed, in which an operator manipulates manipulation means and a slave manipulator is operated in accordance with the manipulation. When a slave manipulator is operated by manipulation means while an object and the slave manipulator are seen with a camera, which comprises observation means, it is sometimes desirable to operate not only the slave manipulator but also the camera itself.

In the case where a slave manipulator being operated is one in number, there is a method, in which manipulation means associated with the slave manipulator is manipulated by the right hand and manipulation means associated with a camera is moved by the left hand. Also, a system is developed, in which in the case where two slave manipulators are operated by two associated manipulation means with the use of the both hands, the hands are separated from the manipulation means and the manipulation means associated with a camera is manipulated.

However, there are some cases where a speed of manipulation is demanded and it is not desirable to separate a hand or hands from manipulation means, which is being manipulated. In this case, means for moving a camera without using a hand or hands in manipulation is contrived as in JP-A-7-328016, JP-A-7-328971, etc. In JP-A-7-328016, while a picture is presented by a head mounted display, a position of the head mounted display is detected, and a camera visual field is changed according to movements of the head. JP-A-7-328971 discloses a manipulator with a TV camera, in which the camera is mounted to the manipulator whereby it is possible to automatically move the manipulator to a position suited to a work to smoothly carry out a work.

Also, means for associating movements of a working tool in an image photographed by a camera with the relationship of a manipulation input device is contrived in JP-A-7-328016 and Japanese Patent No. 3766805. JP-A-7-328016 discloses support of manipulation performed by superimposing an operation coordinate system of a manipulator on a screen, on which a camera image is displayed. Japanese Patent No. 3766805 discloses to conform a direction of motion of a manipulator displayed on an image to direction of motion of a manipulation input device.

As described above, since a master-slave manipulator system using a camera involves a limit in camera visual field, it is frequently desirable to change a camera visual field depending upon movements of a work object and a change in situation.

When a camera is to be changed in position, however, the related art involves a problem that a slave manipulator working portion goes out of a screen, and an agreement in position and orientation between the slave manipulator working portion projected onto display means and manipulation means is not taken account of after a visual field is changed, so that a master-slave operation is hard to perform after the visual field is changed.

Also, when a pointer on GUI (Graphical User Interface) is to be moved by a mouse, it is desired that manipulation means can perform manipulation (referred below to as clutch manipulation) of lifting the mouse in the air when a limit of a manipulating range of the mouse is reached, moving the mouse to a position of easy manipulation, and then again moving the pointer on GUI. That is, there is caused a problem in a limit of a moving range of manipulation means and it is desirable to perform a clutch manipulation, in which manipulation means is returned to a position for easy movement, while a position of a slave manipulator is left as it is. In the case where such clutch manipulation is performed, there is caused a problem that the slave manipulator projected onto display means and manipulation means disagree in position and orientation with each other whereby a direction, in which manipulation is performed by the manipulation means, and a direction, in which the manipulator is moved, disagree with each other. Such disagreement in direction of movement increases a load on an operator to make it difficult to perform a complex operation.

Further, there is also caused a problem that while a visual field is changed, a slave manipulator, which carries out a work, is suspended to lead to worsening in working efficiency and extending in working hour. In particular, in a medical field in recent years, there is spread a low invasion surgery, in which in order to reduce a load on a patient's body, a small hole is formed on a patient's body, a surgical tool and an endoscope are inserted therefrom to perform medical treatment while observing states of an affected part and the surgical tool in endoscope image. In a surgical operation with the use of a slave manipulator, a tool of the slave manipulator is likewise inserted from a small incised part to perform medical treatment on the basis of an endoscope image. In such situation, a manipulation method imposing a load on an operator is not preferred because of a limit in degree of freedom and so it is desirable to readily realize a motion of a slave manipulator, which reflects an operator's will exactly.

In JP-A-7-328016 described above, a camera visual field is changed without the use of both hands but no consideration is taken with respect to disagreement in position and orientation between the hand, which grips a master, after a visual field is changed and a slave manipulator working portion seen in a screen.

In JP-A-7-328971 described above, it is thought that a camera always photographs a slave manipulator but no consideration is taken with respect to the relationship between a slave manipulator displayed on display means and manipulation means.

Japanese Patent No. 3766805 described above discloses an agreement in direction of motion between a surgical manipulator and remote manipulation means but no mention is made of means for moving an endoscope picture and an agreement between a direction of movement of a manipulator on a displayed picture at that time and a method of manipulating manipulation means. Also, no consideration is taken with respect to clutch manipulation.

That is, such related art involves a problem that when a camera visual field is changed and clutch manipulation is begun, a difference in orientation between a slave manipulator working portion photographed by a camera and manipulation means is generated to make it hard to perform manipulation.

SUMMARY OF THE INVENTION

It is an object of the invention to provide a master-slave manipulator system capable of shifting to a master-slave operation, in which even when clutch manipulation is performed or a camera visual field is moved, the relationship in position and orientation between a slave manipulator working portion projected onto a camera image and manipulation means is maintained and the manipulation means can be manipulated intuitively.

That is, it is a first object of the invention to provide a master-slave manipulator system, in which even when clutch manipulation is performed to move a position of manipulation means, manipulation means can be readily manipulated while seeing display means and which is excellent in safety, workability, and operability.

It is a second object of the invention to provide a master-slave manipulator system, in which even when a camera visual field is changed, manipulation means can be readily manipulated while seeing display means and which is excellent in safety, workability, and operability.

It is a third object of the invention to provide a master-slave manipulator system, in which even when clutch manipulation is performed and a camera visual field is changed, manipulation means can be readily manipulated while seeing display means and which is excellent in safety, workability, and operability.

It is a fourth object of the invention to provide a master-slave manipulator system, in which while a camera visual field is changed, it is possible to manipulate a manipulator without confusing an operator and to carry out a change in visual field and manipulation of the manipulator conforming to an operator's will at a time, and which is excellent in safety, workability, and operability.

A first embodiment of the invention, which attains the first object, resides in a master-slave manipulator system comprising: manipulation means that is manipulated in order to create an operation command; a manipulation means control section that reads the operation command to forward a first control command; a manipulator control section, by which a second control command for controlling of respective joints of a slave manipulator is output on the basis of the first control command; the slave manipulator that operates on the basis of the second control command; observation means that observes a motion of the slave manipulator; visual field changing means that changes a visual field of the observation means; a visual field change control section that controls the visual field changing means; and display means that displays an image of the manipulator observed by the observation means on a screen, and further comprising: mode switching means for switching between a master-slave mode, in which the slave manipulator is controlled, and an observation means visual field tracking clutch mode, in which transmission of an operation command to the slave manipulator from the manipulation means is cut off to move the manipulation means to an optional position and orientation; a switching unit control section that reads a signal of the mode switching means to forward a mode signal to the manipulation means control section; and a visual field transform section that forwards a third control command to the manipulator control section and forwards a fourth control command to the visual field change control section on the basis of an operation command read by the manipulation means control section at the time of the observation means visual field tracking clutch mode so as to make an agreement between a direction of motion of an image of the slave manipulator displayed on the display means and a direction of manipulation of the manipulation means.

A second embodiment of the invention, which attains the second object, resides in a master-slave manipulator system comprising: manipulation means that is manipulated in order to create an operation command; a manipulation means control section that reads the operation command to forward a first control command; a manipulator control section, by which a second control command for controlling of respective joints of a slave manipulator is output on the basis of the first control command; the slave manipulator that operates on the basis of the second control command; observation means that observes a motion of the slave manipulator; visual field changing means that changes a visual field of the observation means; a visual field change control section that controls the visual field changing means; and display means that displays an image of the manipulator observed by the observation means on a screen, and further comprising: mode switching means for switching between a master-slave mode, in which an object operated by the manipulation means comprises the slave manipulator, and an observation means visual field tracking master-slave mode, in which an object operated by the manipulation means comprises the slave manipulator and an observation means visual field; a switching unit control section that reads a signal of the mode switching means to forward a mode signal to the manipulation means control section; and a visual field transform section that forwards a third control command to the manipulator control section and forwards a fourth control command to the visual field change control section on the basis of an operation command at the time of the observation means visual field tracking master-slave mode so as to make an agreement between a direction of motion of an image of the slave manipulator displayed on the display means and a direction of manipulation of the manipulation means.

A third embodiment of the invention, which attains the third object, resides in a master-slave manipulator system comprising: manipulation means that is manipulated in order to create an operation command; a manipulation means control section that reads the operation command to forward a first control command; a manipulator control section, by which a second control command for controlling of respective joints of a slave manipulator is output on the basis of the first control command; the slave manipulator that operates on the basis of the second control command; observation means that observes a motion of the slave manipulator; visual field changing means that changes a visual field of the observation means; a visual field change control section that controls the visual field changing means; and display means that displays an image of the manipulator observed by the observation means on a screen, and further comprising: mode switching means for switching among a master-slave mode, in which the slave manipulator is controlled, an observation means visual field tracking clutch mode, in which transmission of an operation command to the slave manipulator from the manipulation means is cut off to move the manipulation means to an optional position and orientation, and an observation means visual field tracking master-slave mode, in which an object operated by the manipulation means comprises an observation means visual field, a switching unit control section that reads a signal of the mode switching means to forward a mode signal to the manipulation means control section; and a visual field transform section that forwards a third control command to the manipulator control section and forwards a fourth control command to the visual field change control section on the basis of an operation command read by the manipulation means control section at the time of the observation means visual field tracking clutch mode so as to make an agreement between a direction of motion of an image of the slave manipulator displayed on the display means and a direction of manipulation of the manipulation means.

A fourth embodiment of the invention, which attains the fourth object, adds to the first or second or third embodiment of the invention a feature that double-arm manipulation means is used as the manipulation means, and two or more manipulators are used as the slave manipulator, and in the observation means visual field tracking clutch mode, zooming-out and zooming-in of a visual field by the observation means are realized in accordance with positive and negative of a differential of a distance between position command input portions of the double-arm manipulation means.

With the master-slave manipulator system of the invention, it is possible to shift to a master-slave operation, in which even when clutch manipulation is performed or a camera visual field is moved, the relationship in position and orientation between a slave manipulator working portion projected onto a camera image and manipulation means is maintained and the manipulation means can be manipulated intuitively.

Other objects, features, and advantages of the present invention will become more apparent from the following description of the embodiment of the invention when taken in conjunction with the accompanying drawings.

BRIEF DESCRIPTION OF THE DRAWINGS

FIG. 6 is a view showing combinations of mode switching in the embodiment;

DESCRIPTION OF THE PREFERRED EMBODIMENT

An embodiment of a master-slave manipulator system according to the invention will be described taking the case of an operation support system with reference to FIGS. 1 to 12.

Figure 1:
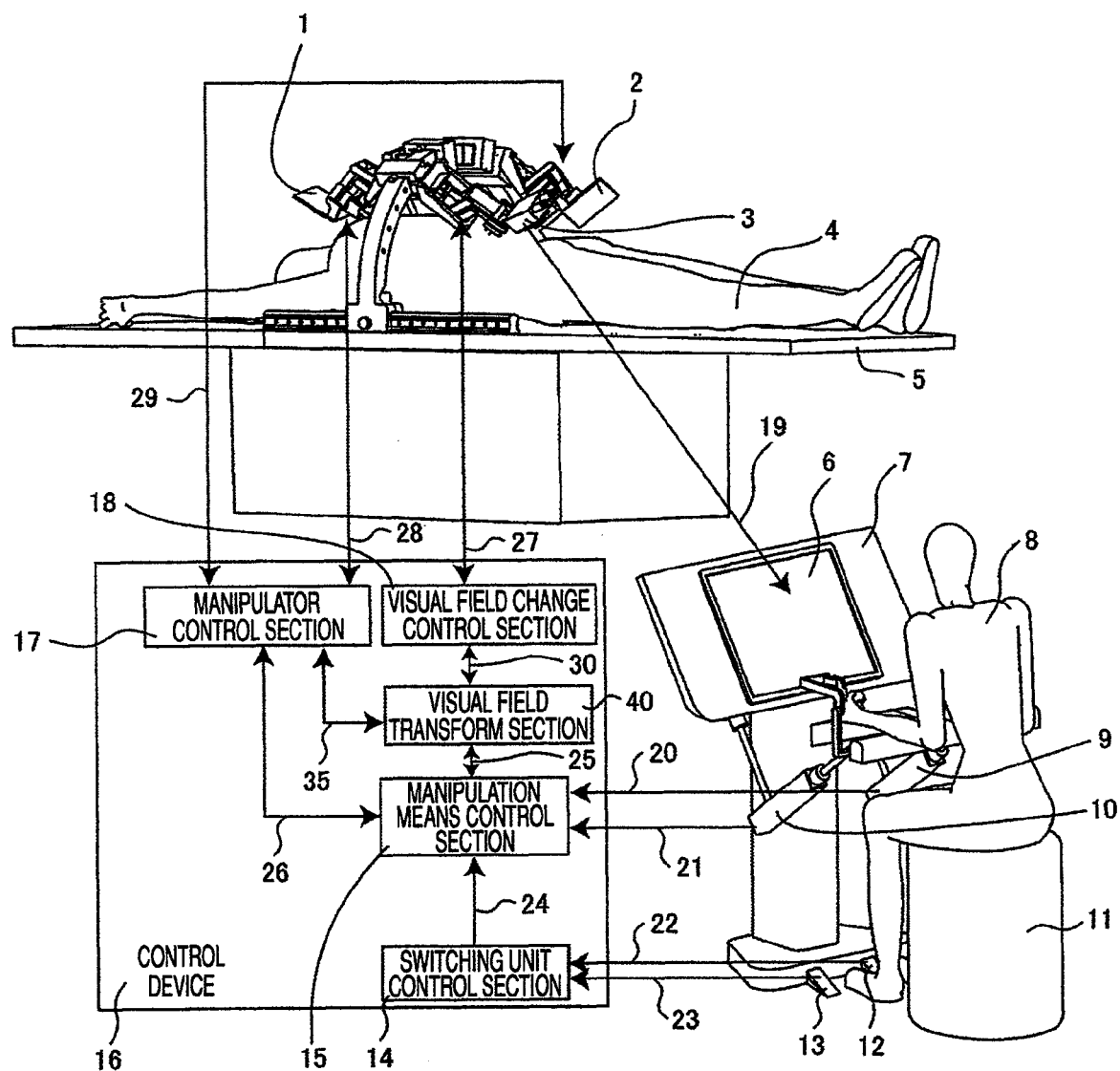
FIG. 1 is a view showing a whole construction of a master-slave manipulator system according to an embodiment of the invention.

First, the whole master-slave manipulator system will be described with reference to FIG. 1. FIG. 1 is a view showing the whole construction of the master-slave manipulator system according to an embodiment of the invention.

A patient 4 is arranged on an operating table 5. Slave manipulators 1, 2 and an endoscope manipulator 3, which are mounted above the operating table 5, are arranged to be directed toward an affected part of the patient 4. The endoscope manipulator 3 is constructed such that an endoscope being observation means is held by a manipulator, which serves as endoscope visual field changing means. A picture imaged by the endoscope held by the endoscope manipulator 3 passes through a transmission path 19 to be displayed on a monitor 6 being display means arranged on a master console 7. While seeing the monitor 6, an operator 8 operates effectors of the slave manipulators 1, 2, which are projected onto the monitor 6, with the use of master devices 9, 10 being manipulation means mounted to the master console 7.

Amounts of motion of the master devices 9, 10 are forwarded to a manipulation means control section 15 through transmission paths 20, 21.

The present system comprises, as switching units, two ON/OFF foot switches, that is, a master-slave mode switching unit 12 and an endoscope mode switching unit 13. Detailed description of modes of the switching units will be given later. In addition, it is unnecessary to divide the switching units into two.

ON/OFF information of the master-slave mode switching unit 12 is forwarded to a switching unit control section 14 through a transmission path 22. When the master-slave mode switching unit 12 is made ON, a master-slave mode is selected by the switching unit control section 14 and information to the effect that the master-slave mode is made ON is forwarded to the manipulation means control section 15 through a transmission path 24 from the switching unit control section 14. Thereby, information of amounts of motion of the master devices 9, 10 is subjected to appropriate coordinate transformation in the manipulation means control section 15 and then is forwarded to a manipulator control section 17 through a transmission path 26.

The manipulator control section 17 solves the inverse kinematics so that the slave manipulators 1, 2 move in accordance with motions of the master devices 9, 10, and forwards control commands of respective joints of the manipulators as calculated to the slave manipulators 1, 2 through transmission paths 28, 29 to control motions of the slave manipulators 1, 2. Respective joint values of the slave manipulators 1, 2 are acquired from encoders (not shown) to be forwarded to the manipulator control section 17 through the transmission paths 28, 29 to be used in control.

ON/OFF information of the endoscope mode switching unit 13 is forwarded to the switching unit control section 14 through a transmission path 23. When the endoscope mode switching unit 13 is made ON, an endoscope mode is selected by the switching unit control section 14 and information to the effect that the endoscope mode is made ON is forwarded to the manipulation means control section 15 through the transmission path 24 from the switching unit control section 14. Thereby, manipulation command values by the master devices 9, 10 are forwarded through a transmission path 25 to a visual field transform section 40 and a command value for movement of an endoscope visual field is calculated so that the relationship in position and orientation between tip ends of the slave manipulators 1, 2 displayed on the monitor 6 and the relationship in position and orientation between the master devices 9, 10 agree with each other, that is, directions of manipulation by the master devices 9, 10 and directions of motion of the tip ends of the slave manipulators 1, 2 agree with each other, and forwarded to a visual field change control section 18. At the same time, a manipulator tip end orientation command value is forwarded to the manipulator control section 17 through a transmission path 35 from the manipulation means control section 15 so as to enable accommodating a change in orientation of the endoscope. The visual field change control section 18 calculates the inverse kinematics to calculate respective joint values of the endoscope manipulator 3 to motion-control the endoscope manipulator 3.

In FIG. 1, a single control device 16 includes the switching unit control section 14, the manipulation means control section 15, the visual field change control section 18, the manipulator control section 17, and the visual field transform section 40 but it may be divided into a plurality of control devices. In addition, detailed contents executed by the visual field transform section 40 will be described with reference to FIG. 3 and the subsequent drawings.

Figure 2:
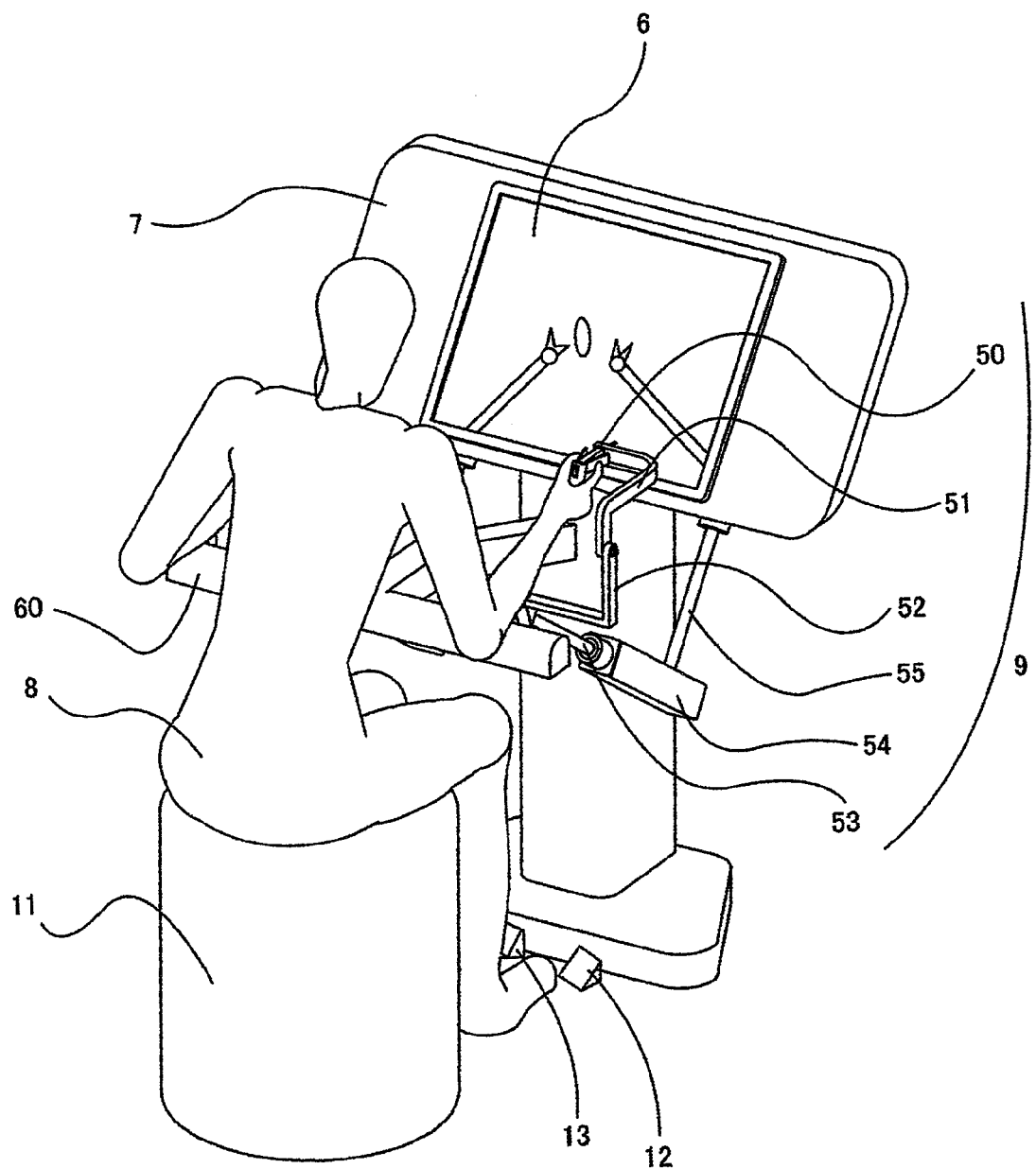
FIG. 2 is a perspective view showing that manner in the embodiment, in which an operator uses a master device mounted to a master console to manipulate manipulators.

Subsequently, the master console 7 will be described specifically with reference to FIG. 2. FIG. 2 is a perspective view showing that manner in the embodiment, in which an operator 8 operates the slave manipulators 1, 2, 3 with the use of the master device 9 mounted to the master console 7.

The operator 8 sits on a chair 11 to put elbows or fore-arms on an armrest 60 to grip an input device gripping portion 50 being an input interface of the master device 9. By seeing the monitor 6 to move the input device gripping portion 50, it is possible to move terminal portions of the slave manipulators 1, 2 displayed on the monitor 6, or the endoscope manipulator 3, which forwards a picture to the monitor 6. In addition, the monitor 6 is preferably a three-dimensional stereo monitor but may be a two-dimensional display monitor.

The input device gripping portion 50 is coupled to the master console 7 through a moving mechanism such as links 51, 52, a rod 53 a rod translational bearing 54, a rod 55, a xy table (not shown), etc. The respective members are coupled together as a rotational joint or a translational joint, respective joint values can be acquired by encoders or potentiometers, which are not shown, and by calculating the kinematics of the master device 9, it is possible to operate six degrees of freedom in position and orientation and opening and closing of grippers. While FIG. 2 shows only the master device 9 for a right arm of the operator 8, the same input interface is provided for a left arm. Foot switches, respectively, are arranged as the master-slave mode switching unit 12 and the endoscope mode switching unit 13 on the master console 7.

In addition, while the armrest 60 is mounted extending from a central column of the master console 7, it is arranged so as not to physically interfere with a working range of the master device 9. A command input switch (not shown) is mounted on a member, which connects between the central column of the master console 7 and the armrest 60, and may be made a switch for those switching units, which are arranged as foot switches, in FIG. 2. Also, a switch (not shown) arranged on the input device gripping portion 50 may be made a switch for switching.

The relationship among the input device gripping portions, the monitor, an affected part, tip ends of the manipulators, grippers, and an endoscope visual field will be described with reference to FIG. 3. FIG. 3(a) shows the relationship among an affected part 100, tip ends 104, 108 of the slave manipulators 1, 2, the grippers 102, 106, and the endoscope visual field 110, FIG. 3(b) shows the relationship among an affected part 120, manipulator tip ends 114, 118, and grippers 112, 116, which are displayed on the monitor 6 at that time, and FIG. 3(c) shows the relationship at that time between the input device gripping portion 50, which operates the slave manipulator 1, and an operator's hand 124, which grips the input device gripping portion to manipulate the same, and the relationship at that time between an input device gripping portion 70, which operates the slave manipulator 2, and an operator's hand 128, which grips the input device gripping portion to manipulate the same.

FIG. 3(a) shows how the manipulator tip ends 104, 108 and the grippers 102, 106 are disposed relative to the affected part 100. The grippers 102, 106 being surgical tools are mounted to the manipulator tip ends 104, 108, respectively, positions are prescribed by the manipulator tip ends 104, 108, and orientations are prescribed by the grippers 102, 106. The endoscope manipulator 3 images the affected part 100 and a visual field of the endoscope is virtually indicated by 110 for the sake of understanding.

FIG. 3(b) shows how the affected part 100 is imaged by the endoscope and displayed on the monitor 6. The affected part 100 is projected as an affected part 120 on the monitor 6. The manipulator tip ends 104, 108 and the grippers 102, 106, respectively, are displayed as manipulator tip ends 114, 118 and grippers 112, 116 on the monitor 6.

FIG. 3(c) shows how operator's hands 124, 128 grip the input device gripping portions 50, 70. The relationship in position and orientation between the input device gripping portions 50, 70, and the relationship in position and orientation between the manipulator tip ends 114, 118 and the grippers 112, 116 on the monitor 6 are presented in the same manner according to a scale ratio as set, and the manipulator tip ends 114, 118 and the grippers 112, 116 on the monitor 6 move in the same manner as the input device gripping portions 50, 70.

Since the slave manipulators 1, 2 and the endoscope manipulator 3 are mounted on the same operating table 5 as shown in FIG. 1, poses/positions and orientations of tip ends of the slave manipulators 1, 2 and the endoscope manipulator 3 can be calculated on the same coordinate system when respective coordinate systems and respective origins are caused to agree with a certain point on the operating table 5. Therefore, it is possible to arrange the manipulator tip ends 104, 108 and the input device gripping portions 50, 70 in the same manner in accordance with the relationship in position and orientation and a certain scale ratio. Likewise, it is possible to determine the endoscope manipulator 3 in position and orientation in the same manner as the relationship in position and orientation between the input device gripping portions 50, 70 so that the manipulator tip ends 114, 118 and the grippers 112, 116 are projected onto the monitor 6.

In addition, while respective coordinate systems are caused to agree with each other owing to the construction, in which the slave manipulators 1, 2 and the endoscope manipulator 3 are mounted on the same operating table 5, a method disclosed in Patent No. 3766805 may be used to cause monitor display and input device gripping portions to agree in position and orientation with each other.

Figure 3:
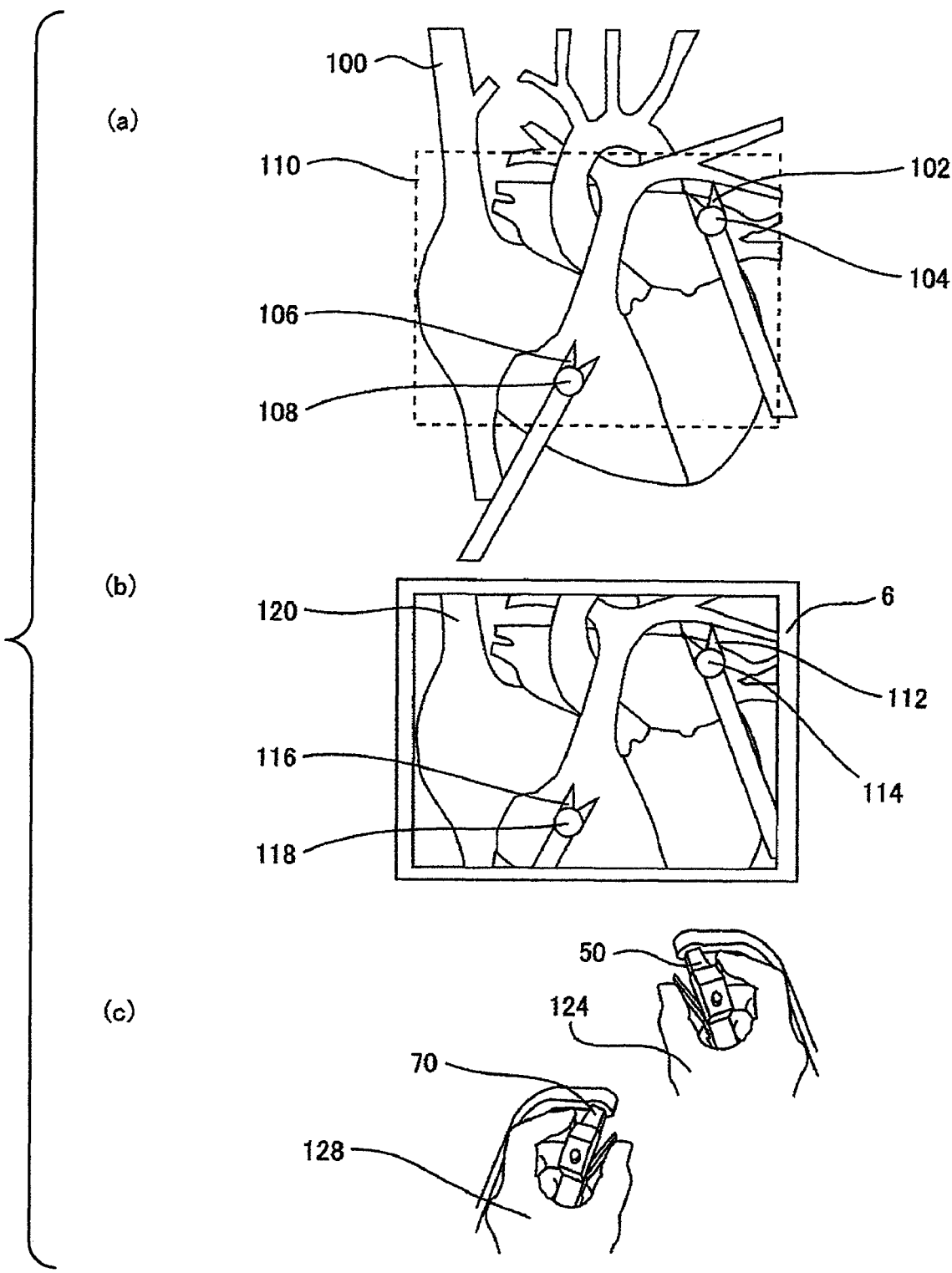
FIG. 3 is views showing the relationship among an affected part, an endoscope visual field, a monitor picture, and input device gripping portions at a certain point of time.

In a state shown in FIG. 3, it is desirable in some cases to return to a position for easy manipulation to perform manipulation on account of a limit on motion of the input device gripping portion 50, or for the reason that an operator's hand 124 projects excessively ahead of an operator's body and an arm cannot be extended further. In this case, there is a demand of cutting off connection of information between a master and a slave, returning the master to a position for easy manipulation without moving the slave, and restarting manipulation (clutch manipulation).

Figure 4:
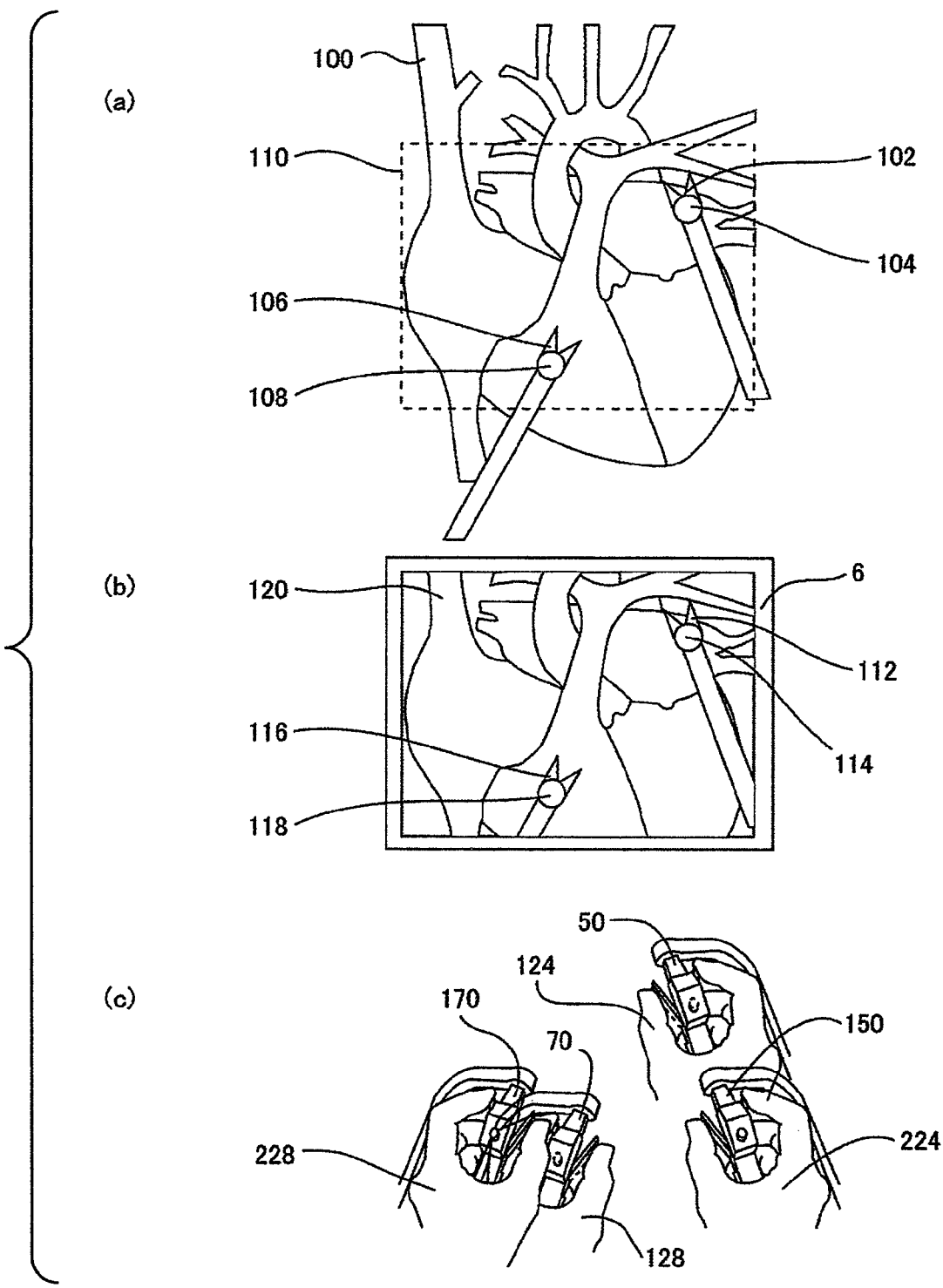
FIG. 4 is views showing the relationship among an affected part, an endoscope visual field, a monitor picture, and input device gripping portions when a clutch manipulation in the related art is performed from a state shown in FIG. 3.

In the prior art, when such motion is carried out, there is brought about a state shown in FIG. 4. In addition, switchover to a clutch mode is made with the use of a foot switch or a switch at hand. FIG. 4(a) shows the relationship among the affected part 100, the manipulator tip ends 104, 108, the grippers 102, 106, and the endoscope visual field 110, FIG. 4(b) shows the relationship at that time among an affected part 120, manipulator tip ends 114, 118, and grippers 112, 116, which are displayed on the monitor 6, and FIG. 4(c) shows the relationship at that time between input device gripping portions 50, 150, 70, 170, which operate the slave manipulators 1, 2, and operator's hands 124, 224, 128, 228, which grip the input device gripping portions to manipulate the same.

In a conventional clutch manipulation, even when masters are moved to positions for easy manipulation, for example, positions of the input device gripping portions 150, 170 and hands 224, 228, which grip the input device gripping portions, from positions of the input device gripping portions 50, 70 and hands 124, 128, which grip the input device gripping portions, as shown in FIG. 4(c), from a state shown in FIG. 3(c), the affected part 100, the manipulator tip ends 104, 108 (FIG. 4(a)), and a manner, in which these elements are projected onto the monitor 6 (FIG. 4(b)), are not changed from those in FIGS. 3(a) and 3(b). When the switching units are again used to make switchover to the master-slave mode from the state, a master-slave motion is made from a state in FIGS. 4(b) and 4(c) but the relationship in position and orientation between operator's hands 224, 228 or the input device gripping portions 150, 170 is different from the relationship in position and orientation between the manipulator tip ends 114, 118, and the grippers 112, 116, which are displayed on the monitor 6, so that there is caused a problem that manipulation is hard to make.

Figure 5:
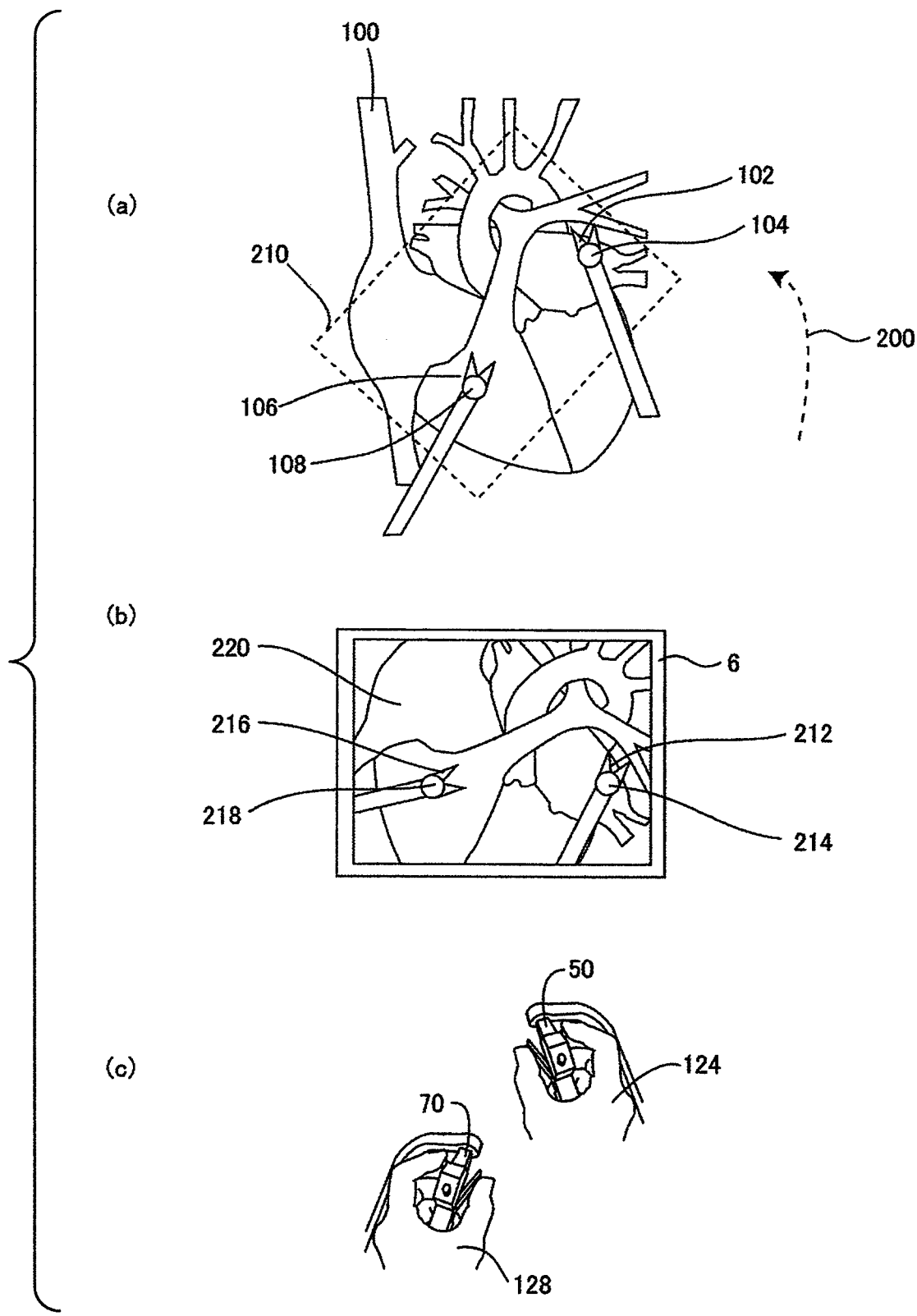
FIG. 5 is views showing the relationship among an affected part, an endoscope visual field, a monitor picture, and input device gripping portions when an endoscope visual field is turned in the related art from a state shown in FIG. 3.

Also, in the case where there is a demand for turning an endoscope visual field from a state in FIG. 3, according to the prior art, an endoscope visual field is turned according to a rotating angle by, for example, a gyrosensor mounted to a head mounted display, or an endoscope visual field is turned as shown in FIG. 5 by manipulation with a device, which corresponds to operation of an endoscope and is other than a master device for manipulation of a manipulator, or operation of an endoscope with speech recognition, or operation of endoscope with a foot switch.

FIG. 5(a) shows the relationship among the affected part 100, the manipulator tip ends 104, 108, the grippers 102, 106, and an endoscope visual field 210, FIG. 5(b) shows the relationship at that time among an affected part 220, manipulator tip ends 214, 218, and grippers 112, 116, which are displayed on the monitor 6, and FIG. 5(c) shows the relationship at that time between input the device gripping portions 50, 70, which operate the slave manipulators 1, 2, and operator's hands 124, 128, which grip the input device gripping portions to manipulate the same.

When the master devices 9, 10 are not moved in position and orientation and the endoscope visual field 210 is moved in a direction indicated by an arrow 200 in FIG. 5(a) by other methods than the operation by the master devices 9, 10, a visual field is moved as indicated by the endoscope visual field 210, the affected part 220 is displayed on the monitor 6, and the manipulator tip ends 214, 218 and the grippers 112, 116 are displayed on the monitor 6. At this time, the manipulator tip ends 214, 218 and the grippers 112, 116 displayed on the monitor 6 are different in position and orientation from the input device gripping portions 50, 70 and operator's hands 124, 128 shown in FIG. 5(c). When master-slave is begun from this state, an uncomfortable feeling in manipulation is generated to cause a problem that manipulation is hard to make.

Here, according to the embodiment, the master devices 9, 10 used for operation of the slave manipulators 1, 2 are used to operate movement of the endoscope visual field or to realize a change in endoscope visual field, which follows the clutch manipulation, whereby when returned to the master-slave mode, the relationship in position and orientation between the manipulator tip ends displayed on the monitor and the input device gripping portions can accommodate to achieve an agreement in direction of motion. This is specifically described below.

A new clutch manipulating mode according to the embodiment is called an endoscope visual field tracking clutch mode. While a mode is switched by the mode switching units 12, 13, two foot switches 12, 13 are made use of as switching units in the embodiment and a mode is switched by respective combinations thereof. FIG. 6 shows combinations of the mode switching units 12, 13.

When the endoscope mode switching unit 13 is put in ON state and the master-slave mode switching unit 12 is made ON as shown in FIG. 6, there is brought about an endoscope visual field tracking master-slave mode, in which an endoscope visual field tracks movements of the slave manipulators 1, 2. When the endoscope mode switching unit 13 is put in ON state and the master-slave mode switching unit 12 is made OFF, there is brought about an endoscope visual field tracking clutch mode. When the endoscope mode switching unit 13 is put in OFF state and the master-slave mode switching unit 12 is made ON, a normal master-slave operation is performed, in which the endoscope visual field is not varied and the slave manipulators 1, 2 are moved according to manipulation of the master devices 9, 10. When the endoscope mode switching unit 13 is put in OFF state and the master-slave mode switching unit 12 is made OFF, there is brought about a mode, in which all connections are cut off and nothing is moved even when the master devices 9, 10 are moved. This mode can be said to be a conventional clutch mode.

In addition, while two foot switches in the embodiment are used to materialize the mode switching units 12, 13, means for mode switchover is not limited to a foot switch.

The endoscope visual field tracking clutch mode described above will be described with reference to FIGS. 7 to 10.

When the master devices 9, 10 are moved in the clutch manipulation to positions for easy manipulation from a state shown in FIG. 3, an operator uses the master-slave mode switching unit 12 to select the endoscope visual field tracking clutch mode. Let assume that hands 124, 128 grip the input device gripping portions 50, 70 and they are moved to positions of input device gripping portions 350, 370 and hands 324, 328 as shown in FIG. 7(c). At this time, encoders (not shown) measure trajectory of position and orientations of the input device gripping portions 350, 370 momentarily, the two input device gripping portions 350, 370, respectively, are calculated with respect to position and orientation, and a travel distance of a midpoint 60 and an angle θ formed by straight lines, which connect between the two input device gripping portions 350, 370, are calculated.

In the case shown in FIG. 7(c), since the input device gripping portions 350, 370 move but the midpoint 60 does not move, an endoscope visual field 310 is turned by an angle θ, which is formed by a virtual, straight line 65 connecting between the input device gripping portions 50, 70 before movement and a virtual, straight line 365 connecting between the input device gripping portions 350, 370 after movement, with a sense of turning reversed as shown in FIG. 7(a). Further, without varying the manipulator tip ends 104, 108, orientations of grippers 302, 306 are moved by an angle θ so that orientations of grippers 312, 316 displayed on the monitor 6 become the same as those of the input device gripping portions 350, 370. Thereby, the relationship in position and orientation between the manipulator tip ends 314, 318 and the grippers 312, 316, which are displayed on the monitor 6, becomes the same in position and orientation between the input device gripping portions 350, 370.

Thereby, even when it is tried to shift to the master-slave motion just after the clutch manipulation, a master-slave operation can be performed without an uncomfortable feeling since hands 324, 328 and the input device gripping portions 350, 370 at the termination of clutch manipulation agree in position and orientation with the manipulator tip ends 314, 318 and the grippers 312, 316, which are displayed on the monitor 6.

Figure 7:
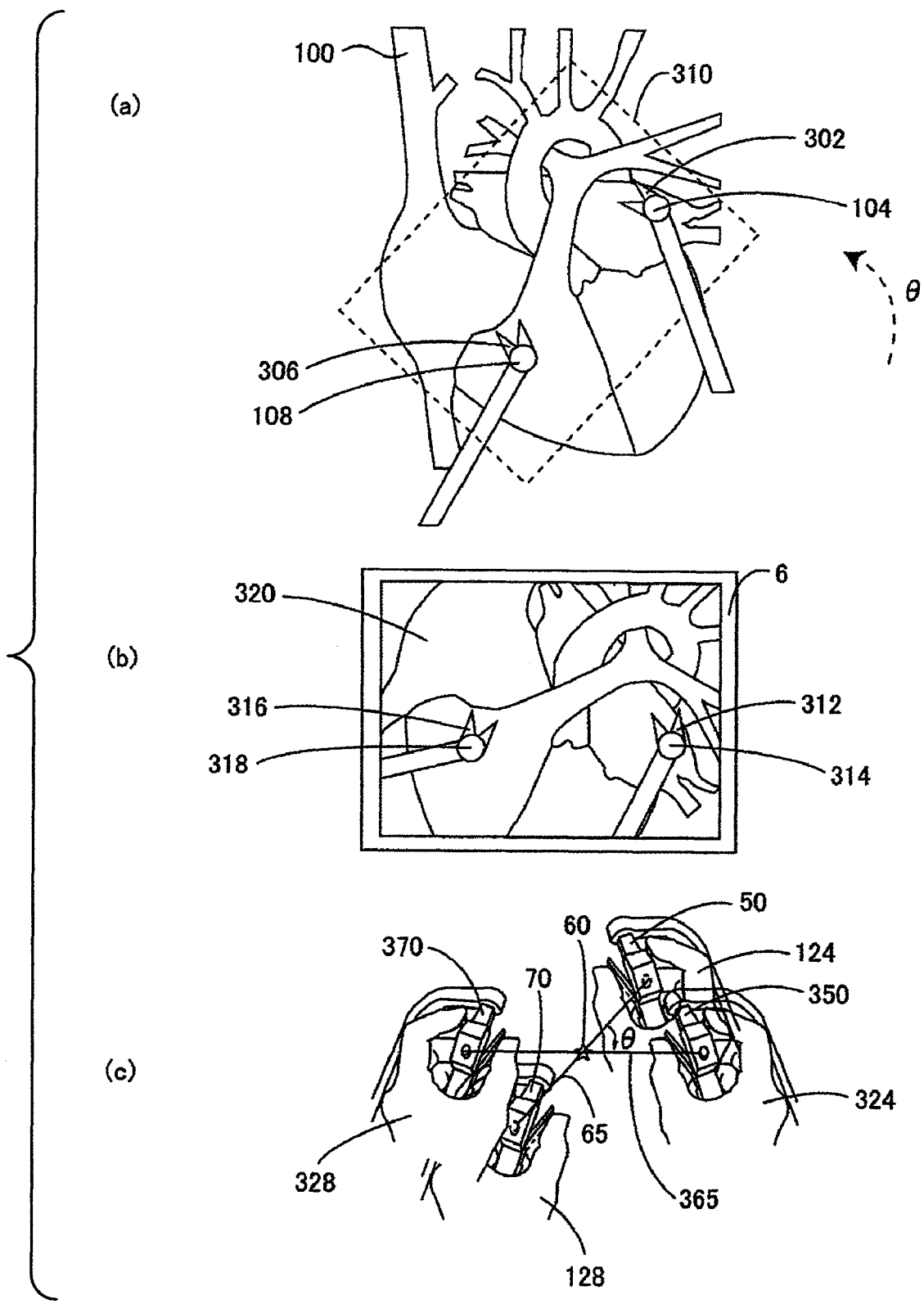
FIG. 7 is views showing an example of the relationship among an affected part, an endoscope visual field, a monitor picture, and input device gripping portions when an endoscope visual field tracking clutch mode in the embodiment is realized from a state shown in FIG. 3.
Figure 8:
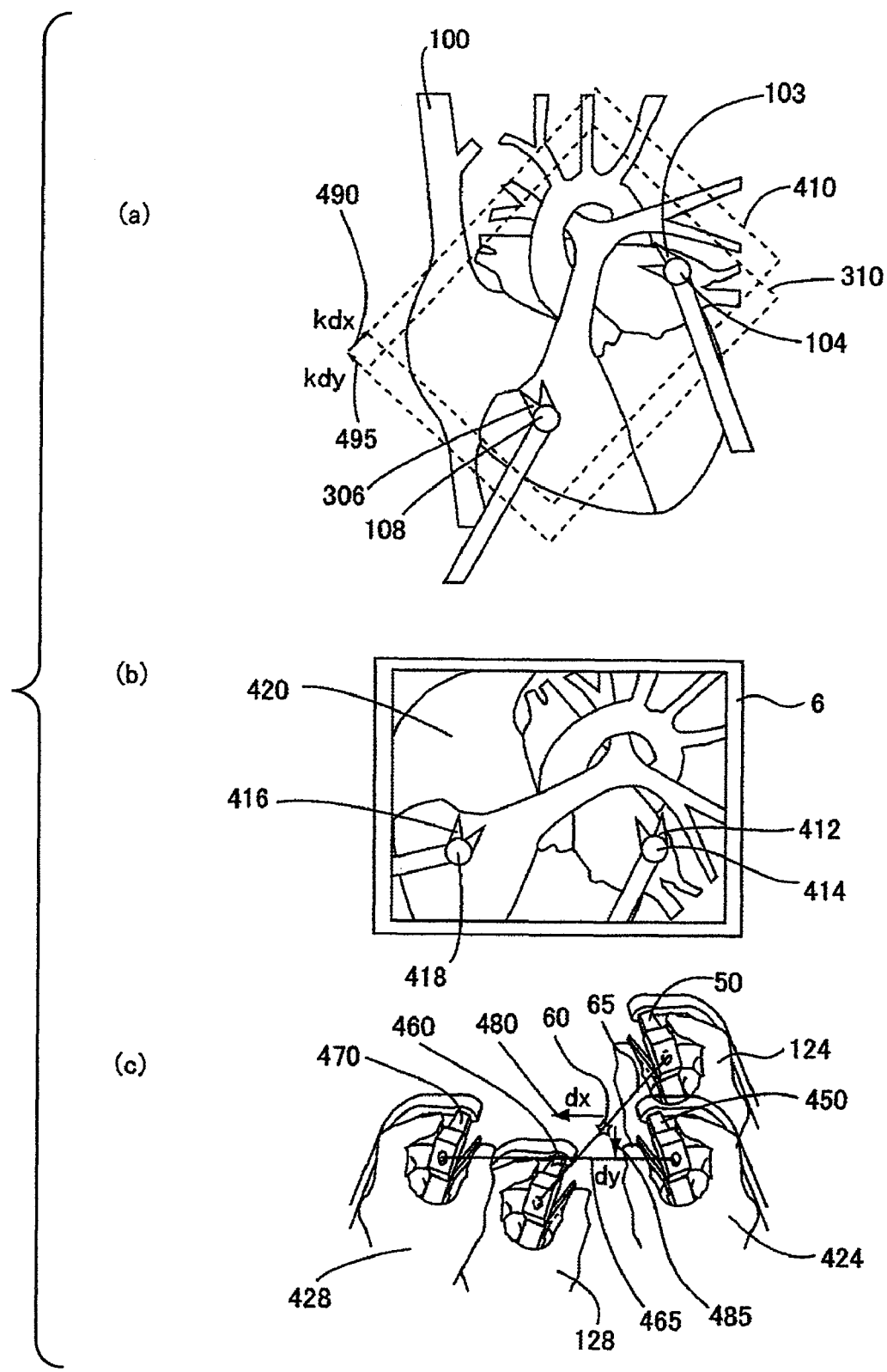
FIG. 8 is views showing a further example of the relationship among an affected part, an endoscope visual field, a monitor picture, and input device gripping portions when an endoscope visual field tracking clutch mode in the embodiment is realized from a state shown in FIG. 3.

Further, when input device gripping portions 450, 470 are moved to positions shown in FIG. 8(c) by operator's hands 424, 428, a virtual, straight line 65 connecting between the input device gripping portions 50, 70 and its midpoint 60 before movement are moved to a virtual, straight line 465 connecting between the input device gripping portions 450, 470 and its midpoint 460 after movement. Differential displacements dx 480 and dy 485 at this time are calculated from encoders (not shown) and the endoscope visual field 310 is moved to an endoscope visual field 410 by travels kdx 490 and kdy 495, which correspond to the values of the displacements as shown in FIG. 8(a). Thereby, the endoscope visual field moves in parallel on the monitor 6 as shown in FIGS. 7(b) to 8(b) and manipulator tip ends 414, 418 and grippers 412, 416 are displayed in position and orientation to correspond to the input device gripping portions 450, 470 in a physical space. In addition, a scale ratio k of a travel of a midpoint of input device gripping portions to a travel of an endoscope visual field can be changed depending upon an affected part being an object and a situation.

Thereby, even when movements of input device gripping portions in clutch manipulation involve rotation and translation (movement in parallel), it is possible to carry out the master-slave operation without an uncomfortable feeling since hands 424, 428 and the input device gripping portions 450, 470 at the termination of clutch manipulation agree in position and orientation with the manipulator tip ends 414, 418 and the grippers 412, 416, which are displayed on the monitor 6, and the both agree in direction of manipulation and direction of motion with each other, when shifted to the master-slave operation after the clutch manipulation.

Figure 9:
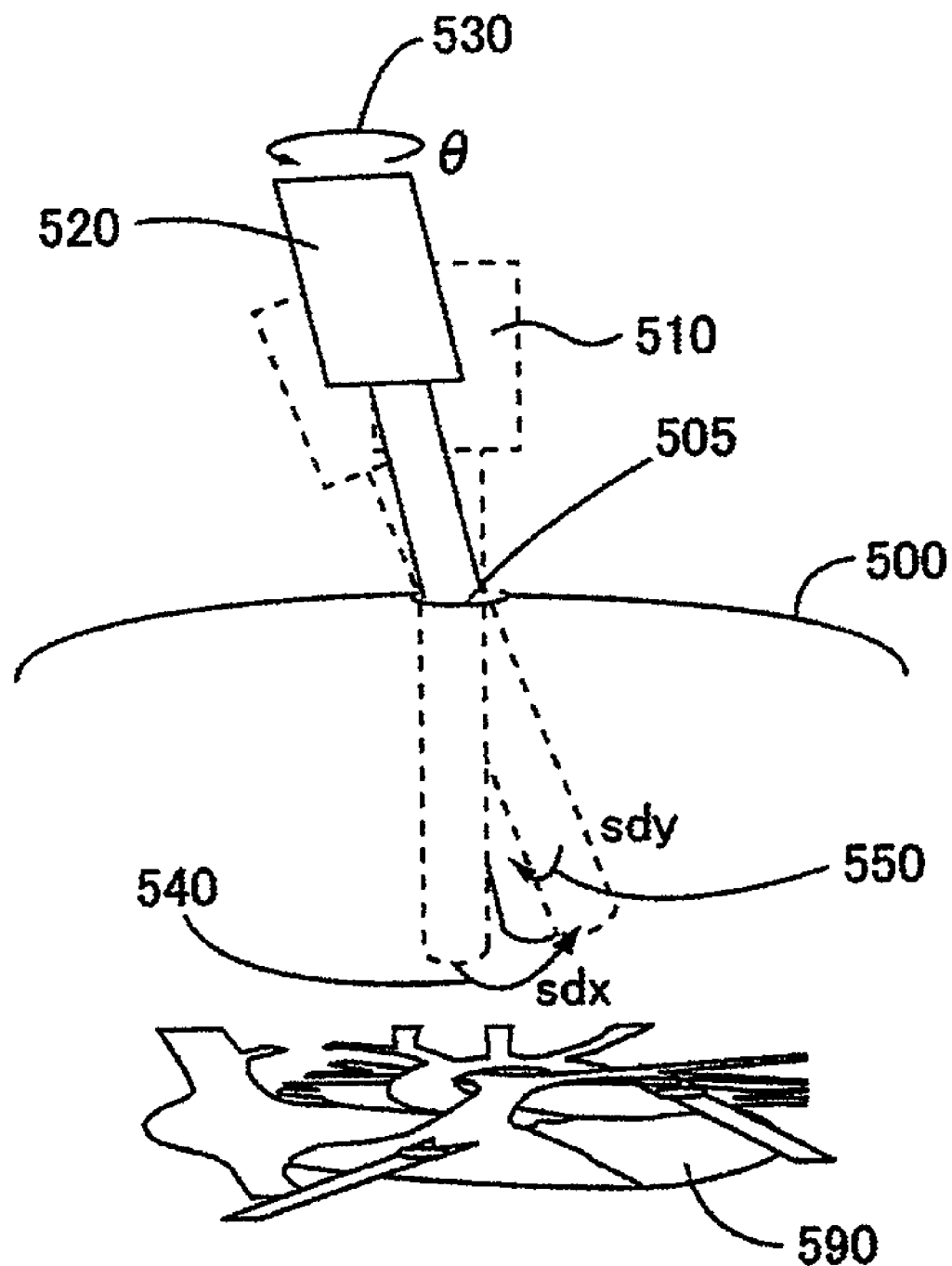
FIG. 9 is a view showing a manner, in which an endoscope constrained by a body surface is moved in the embodiment.
Figure 10:
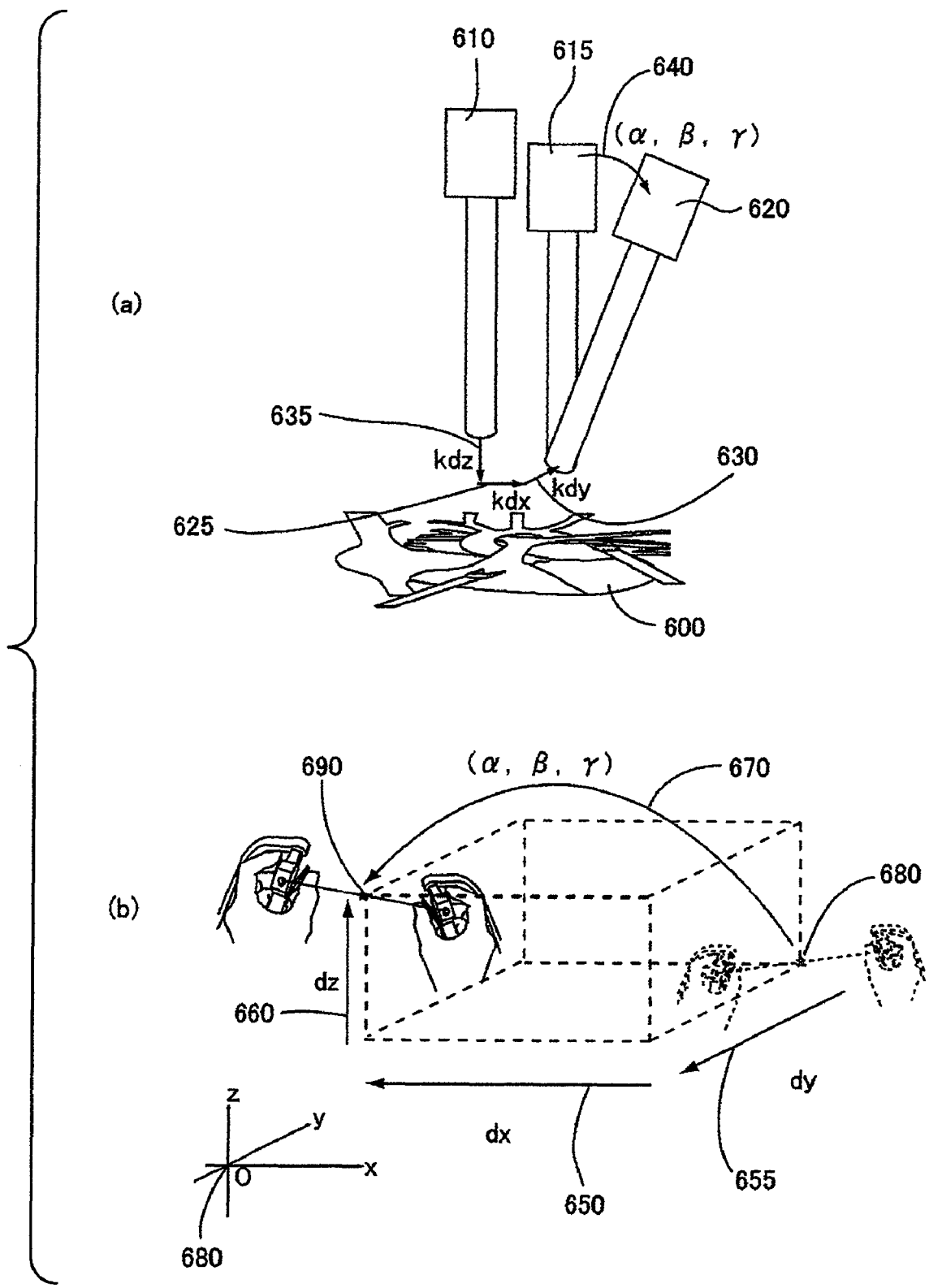
FIG. 10 is views showing the relationship in motion between a camera and input device gripping portions in the embodiment when the camera is not constrained.

FIGS. 9 and 10 illustrate movements of an endoscope or a camera when input device gripping portions are moved. In the case where object observing means comprises an endoscope and an operation with an endoscope is an object, an axis of the endoscope is constrained by a body surface 500 and the endoscope can be moved only in pivotal movement about a body-surface entry point 505 and in axial rotation.

Therefore, movements of the endoscope visual fields 310, 410 illustrated in FIG. 8(a) are changed in visual field by movements of endoscopes 510, 520 shown in FIG. 9. Assuming that 510 indicates a position of the endoscope for realizing a visual field state shown in FIG. 3, the endoscope is moved to a position 520 by amounts of motion sdx 540 and sdy 550, which are obtained by multiplying displacements dx 480 and dy 485 of the input device gripping portions shown in FIG. 8(c) by a coefficient s calculated from a set scale ratio and a zoom ratio of the endoscope, and an affected part 590 is imaged. Also, turning θ of a visual field shown in FIG. 7 is realized by turning an endoscope axis as indicated by an arrow 530 in FIG. 9.

In other cases than an operation with an endoscope, for example, an operation performed in a state, in which a certain measure of hole is formed on the breast, and a master-slave work, which is not limited to an operation and in which a camera visual field is not limited in movement, a visual field can also be changed by translating a camera visual field according to travels dx 650, dy 655, and dz 660 of a midpoint of double-arm input device gripping portions, calculating displacements of an orientation of a line, which connects between the double-arm input device gripping portions, in terms of roll, pitch, and yaw, and moving a camera axis according to an angular differential of the displacements. An embodiment in this case is shown in FIG. 10 and described below.

Let assume that the endoscope visual field tracking clutch mode is selected and displacements when a midpoint 680 of input device gripping portions is moved to a new midpoint 690 are calculated as dx 650, dy 655, and dz 660 in a physical coordinate system 680. Also, roll, pitch, and yaw (α, β, γ) 670 of a change in orientation of a straight line connecting between the input device gripping portions at this time are calculated. Since an orientation of axial turning of the straight line is not determined only by the matter that the straight line connects between the input device gripping portions, however, it may be fixed. On the basis of this information, a camera, which images an object 600, is moved by kdx 625, kdy 630, and kdz 635 according to a motion scale ratio k, and further moved by roll, pitch, and yaw (α, β, γ) 640, which correspond to a change in orientation, whereby the endoscope is moved to 620 from 610. Thereby, an endoscope visual field corresponding not only to translation of manipulation input devices and turning (yaw turning) of an endoscope visual field but also to roll and pitch can be provided on the monitor 6, so that a direction, in which gripping input devices are manipulated, and a direction, in which manipulators on a monitor are moved, are heightened in agreement.

Subsequently, a method, according to the embodiment, in which the relationship in position and orientation between a master and a slave on a monitor is kept and manipulator tip ends are not removed from an endoscope visual field even when an endoscope visual field is changed, will be described with reference to FIGS. 11 and 12. This method is started up when the endoscope visual field tracking master-slave mode illustrated in FIG. 6 is selected.

In the endoscope visual field tracking master-slave mode, an endoscope visual field is also changed while master-slave connection is kept.

Usually, the relationship in position and orientation between slave manipulators on the monitor 6 and input device gripping portions undergoes deviation and a direction of motion and a direction of manipulation do not agree with each other. For turning of an endoscope visual field, the same method as that in the endoscope visual field tracking clutch mode is used to provide for an agreement in position and orientation between manipulators displayed on a monitor and master input device gripping portions as illustrated in FIG. 7.

Figure 11:
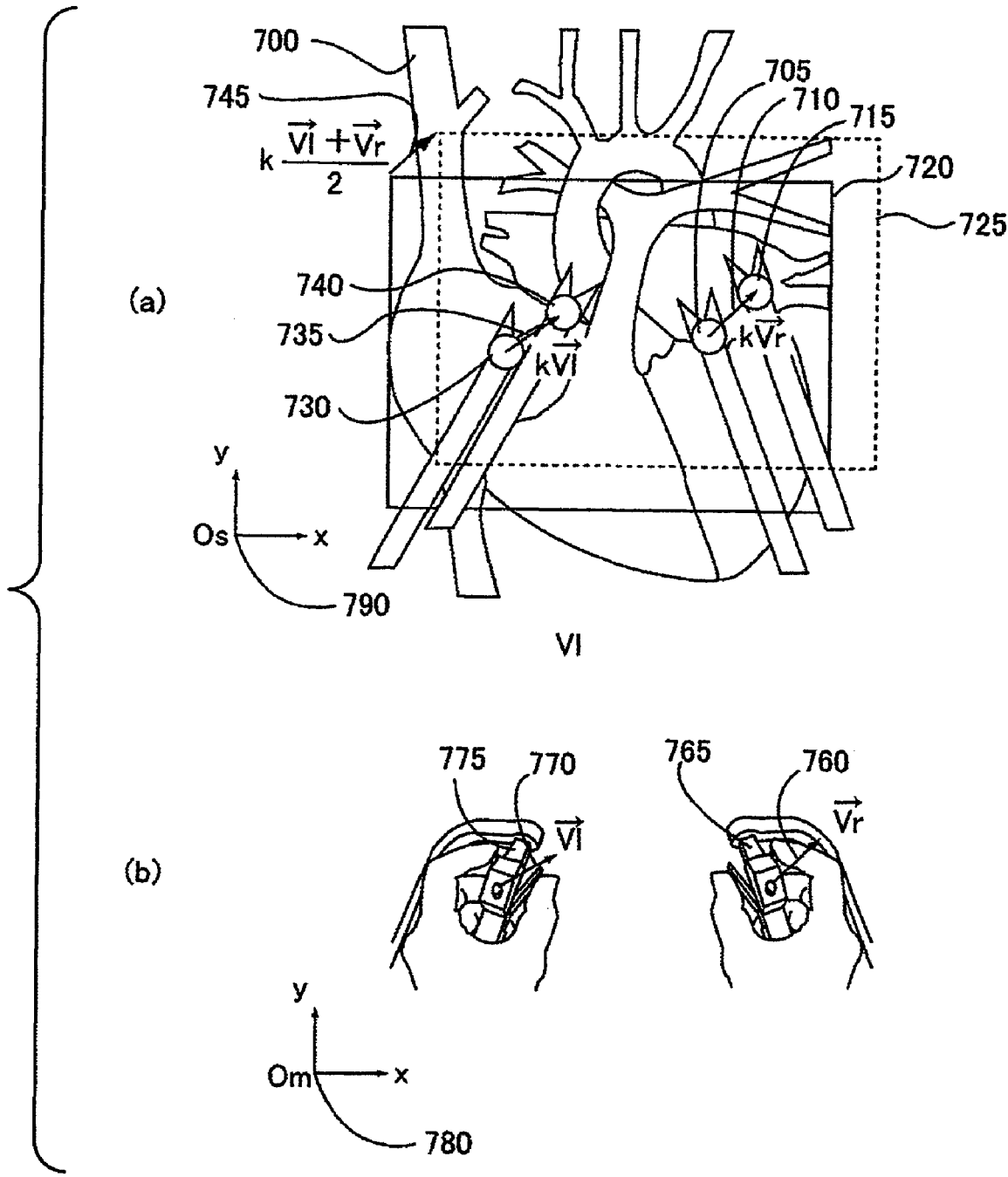
FIG. 11 is views showing a manner, in which movements of input device gripping portions move manipulators and a visual field at a time.
Figure 12:
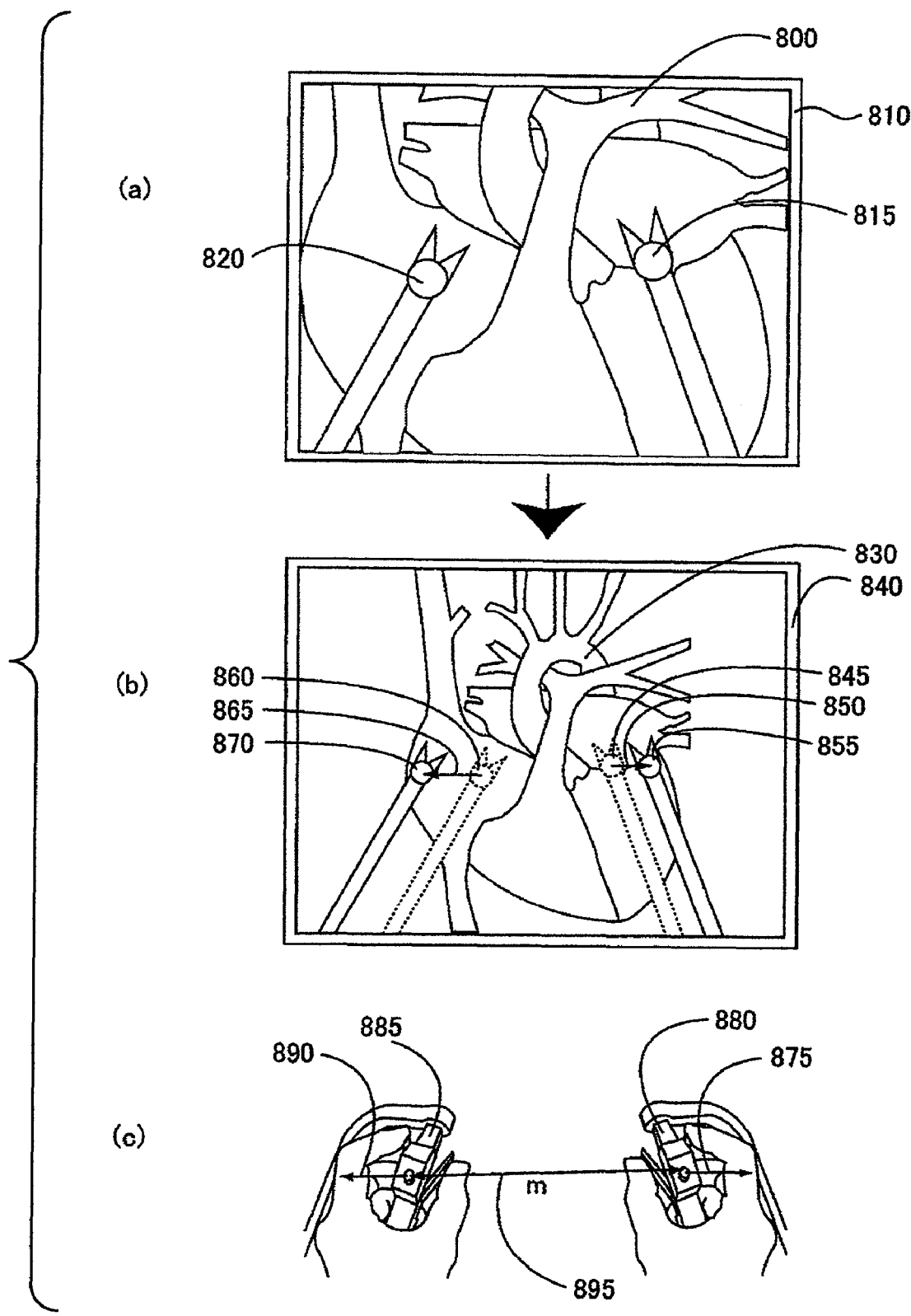
FIG. 12 is views showing a manner, in which movements of grip input devices in the embodiment cause movements of manipulators and zooming of a visual field at a time.

Referring to FIG. 11, an explanation will be given to the case where for translation of an endoscope visual field, the endoscope is constrained by a body surface to enable only planar two-degree-of-freedom direction, direct-acting or a zoom function, and endoscope axial turning. FIG. 11(a) shows a manner, in which an affected part 700 is imaged in an endoscope visual field 720 (represented in a virtual manner for the sake of understanding). FIG. 11(b) shows a manner, in which input device gripping portions behave at this time.

In the endoscope visual field tracking master-slave mode, movement differential vectors Vr 760 and Vl 770 of double-arm input device gripping portions 765, 775 in a physical space plane (of which a coordinate system includes Om 780) corresponding to an endoscope visual field plane (of which a coordinate system includes Os 790 temporarily) are calculated. Slave manipulator tip ends are moved to 715 from 705 and to 740 from 730 by vectors kVr 710 and kVl 735, which are obtained by multiplying the movement differential vectors Vr 760 and Vl 770 by the scale ratio k. At this time, the endoscope visual field 720 is moved by vectors k (Vr+Vl)/2 745 to become an endoscope visual field 725, thereby tracking movements of the manipulator tip ends.

In the case where vectors Vr 875 and Vl 890 are reversed in sense as shown in FIG. 12(c), however, there is conceivable a possibility that an endoscope visual field is not moved and manipulator tip ends are moved in a direction, in which they get out of a screen. Here, as shown in FIG. 12(c), a distance m 895 between two input device gripping portions 880, 885 is calculated, and depending upon positive and negative of a differential Δm of the distance, zoom-in/zoom-out or a motion of approaching an object in endoscope axis translation/going away from an object in endoscope axis translation is performed.

FIG. 12(a) shows a manner, in which an affected part 800 and slave manipulators 815, 820 are displayed on a monitor 810 when the input device gripping portions 880, 885 are held in a state shown in FIG. 12(c). FIG. 12(b) shows a manner, in which an affected part 830 and manipulators 855, 870 are displayed on a monitor 840 when manipulator tip ends 845, 860 in a state shown in FIG. 12(a) are moved in directions 850 and 865 with the use of the endoscope visual field tracking mode and an endoscope picture zooms out.

In the case where a differential Δm of a distance is positive, that is, a distance m 895 between two input device gripping portions is increased, movements of the two input device gripping portions also cause manipulator tip ends to move away from 845 to 855 and from 860 to 870 in directions, in which they go out of an endoscope visual field, that is, a monitor screen. Therefore, in the endoscope visual field tracking master-slave mode, as Δm increases, manipulator tip ends zoom out or move away from an object in endoscope axis translation. Thereby, it is possible to move an endoscope visual field so that manipulator tip ends are displayed on the monitor 840 at all times.

In the case where a differential Δm of a distance is negative, that is, a distance m 895 between two input device gripping portions is decreased, movements of the two input device gripping portions cause manipulator tip ends to approach each other. In this case, the manipulator tip ends move according to the value of Δm so that the endoscope zooms in or approaches an object in endoscope axis translation. A portion, which the manipulator tip ends approach, is an object, of close observation is desired, and the endoscope zooms in to move corresponding to a human's intuition of desiring to see details. In addition, it is assumed that a zoom ratio corresponding to Δm can be appropriately set.

By using the visual field transform section 40 shown in FIG. 1 to perform transformation of an endoscope visual field, it is possible in the endoscope visual field tracking master-slave mode to move an endoscope visual field so that manipulator tip ends do not go out of the monitor 6 while communication is connected between a master and a slave. Thereby, even when an endoscope visual field is changed or clutch manipulation is performed to return to the master-slave mode, it is possible to realize a master-slave operation, in which the relationship in position and orientation between a master and a slave on a monitor is always maintained and which is good in operability and intuitive.

According to the embodiment described above, in a clutch mode selected by the mode switching unit, displacements of manipulation means are measured and an endoscope visual field is moved in accordance with the displacements whereby in the clutch mode, positions of manipulators are not moved and an endoscope visual field is moved so that the positional relationship between the manipulators in an endoscope picture displayed on a monitor and the positional relationship between input device gripping portions of the manipulation means become the same. Further, grippers of the manipulators are moved so that the grippers mounted to manipulator tip ends are made the same in orientation as the input device gripping portions whereby the grippers displayed on the monitor are made the same in orientation as the input device gripping portions, so that the input device gripping portions and the manipulators displayed on the monitor are kept in position and orientation at all times to enable an intuitive manipulation at all times because of an agreement in a direction of motion even when shifted to the master-slave mode from the clutch mode.

That is, a favorable visual field can be presented to an operator by providing means, in which even when a camera visual field is changed and even when a master is changed in position and orientation by clutch manipulation, slave manipulator working portions projected onto display means and manipulation means correspond in position and orientation to each other and can be moved with an agreement in directions of motion immediately after being shifted to the master-slave mode. By providing a favorable visual field, the manipulator system is improved in operability and an operation of the manipulator system can be improved in safety. Also, labor required for achieving an agreement in position and orientation between manipulators on display means and manipulation means is omitted, operation time of the manipulator system is shortened, and an improvement in working efficiency can be achieved. Also, since it becomes unnecessary to arrange an actuator on manipulation means and to give a force to the manipulation means to achieve a change in position and orientation so as to correspond in position and orientation to manipulators on display means, a manipulation means apparatus can be made small in size. Also, since there is no need for an actuator therefor, the manipulation means apparatus is inexpensive and safe without a fear that an operator suffers damage at the time of an unexpected error.

In addition, the technology in the conventional art involves a problem that working hour is extended because manipulators, which perform work on an object, cannot work and are suspended while an endoscope visual field is moved. However, with the use of the present embodiment, manipulators can be moved together with movement of an endoscope visual field, so that there are achieved an improvement in working efficiency and shortening in working hour. Also, a conventional clutch mode can be selected by a switching unit whereby the clutch manipulation can be performed without movement of an endoscope visual field and proper use of operators depending upon a situation is enabled to eliminate worsening in operability.

While the descriptions have been given with respect to the embodiment, it is apparent to those skilled in the art that the invention is not limited thereto but various changes and modifications can be made within the spirit of the invention or the scope as defined by the appended claims.

The invention claimed is:

1. A master-slave manipulator system comprising:
   manipulation means that is manipulated in order to create an operation command;
   a manipulation means control section that reads the operation command to forward a first control command;
   a manipulator control section, by which a second control command for controlling of respective joints of a slave manipulator is output on the basis of the first control command;
   the slave manipulator that operates on the basis of the second control command;
   observation means that observes a motion of the slave manipulator;
   visual field changing means that changes a visual field of the observation means;
   a visual field change control section that controls the visual field changing means;
   display means that displays an image of the manipulator observed by the observation means on a screen;
   mode switching means for switching between a master-slave mode, in which the slave manipulator is controlled, and an observation means visual field tracking clutch mode, in which transmission of an operation command to the slave manipulator from the manipulation means is cut off to move the manipulation means to an optional position and orientation;

a switching unit control section that reads a signal of the mode switching means to forward a mode signal to the manipulation means control section; and a visual field transform section that forwards a third control command to the manipulator control section and forwards a fourth control command to the visual field change control section on the basis of an operation command read by the manipulation means control section at the time of the observation means visual field tracking clutch mode so as to make an agreement between a direction of motion of an image of the slave manipulator displayed on the display means and a direction of manipulation of the manipulation means.

2. A master-slave manipulator system comprising:

manipulation means that is manipulated in order to create an operation command;

a manipulation means control section that reads the operation command to forward a first control command;

a manipulator control section, by which a second control command for controlling of respective joints of a slave manipulator is output on the basis of the first control command;

the slave manipulator that operates on the basis of the second control command;

observation means that observes a motion of the slave manipulator;

visual field changing means that changes a visual field of the observation means;

a visual field change control section that controls the visual field changing means;

display means that displays an image of the manipulator observed by the observation means on a screen;

mode switching means for switching between a master-slave mode, in which an object operated by the manipulation means comprises the slave manipulator and the observation means, and an observation means visual field tracking master-slave mode, in which an object operated by the manipulation means comprises an observation means visual field;

a switching unit control section that reads a signal of the mode switching means to forward a mode signal to the manipulation means control section; and a visual field transform section that forwards a third control command to the manipulator control section and forwards a fourth control command to the visual field change control section on the basis of an operation command at the time of the observation means visual field tracking master-slave mode so as to make an agreement between a direction of motion of an image of the slave manipulator displayed on the display means and a direction of manipulation of the manipulation means.

3. A master-slave manipulator system comprising:

manipulation means that is manipulated in order to create an operation command;

a manipulation means control section that reads the operation command to forward a first control command;

a manipulator control section, by which a second control command for controlling of respective joints of a slave manipulator is output on the basis of the first control command;

the slave manipulator that operates on the basis of the second control command;

observation means that observes a motion of the slave manipulator;

visual field changing means that changes a visual field of the observation means;

a visual field change control section that controls the visual field changing means;

display means that displays an image of the manipulator observed by the observation means on a screen;

mode switching means for switching among a master-slave mode, in which the slave manipulator is controlled, an observation means visual field tracking clutch mode, in which transmission of an operation command to the slave manipulator from the manipulation means is cut off to move the manipulation means to an optional position and orientation, and an observation means visual field tracking master-slave mode, in which an object operated by the manipulation means comprises the slave manipulator and an observation means visual field;

a switching unit control section that reads a signal of the mode switching means to forward a mode signal to the manipulation means control section; and a visual field transform section that forwards a third control command to the manipulator control section and forwards a fourth control command to the visual field change control section on the basis of an operation command read by the manipulation means control section at the time of the observation means visual field tracking clutch mode so as to make an agreement between a direction of motion of an image of the slave manipulator displayed on the display means and a direction of manipulation of the manipulation means.

4. The master-slave manipulator system according to claim 1, wherein double-arm manipulation means is used as the manipulation means, and two or more manipulators are used as the slave manipulator, and in the observation means visual field tracking clutch mode, zooming-out and zooming-in of a visual field by the observation means are realized in accordance with positive and negative of a differential of a distance between position command input portions of the double-arm manipulation means.

5. The master-slave manipulator system according to claim 2, wherein double-arm manipulation means is used as the manipulation means, and two or more manipulators are used as the slave manipulator, and in the observation means visual field tracking clutch mode, zooming-out and zooming-in of a visual field by the observation means are realized in accordance with positive and negative of a differential of a distance between position command input portions of the double-arm manipulation means.

6. The master-slave manipulator system according to claim 3, wherein double-arm manipulation means is used as the manipulation means, and two or more manipulators are used as the slave manipulator, and in the observation means visual field tracking clutch mode, zooming-out and zooming-in of a visual field by the observation means are realized in accordance with positive and negative of a differential of a distance between position command input portions of the double-arm manipulation means.

* * * * *